(12) United States Patent
Soga et al.

(10) Patent No.: US 10,527,545 B2
(45) Date of Patent: Jan. 7, 2020

(54) TOTAL REFLECTION MEASUREMENT DEVICE

(71) Applicant: JASCO Corporation, Tokyo (JP)

(72) Inventors: Noriaki Soga, Tokyo (JP); Hiroshi Sugiyama, Tokyo (JP); Jun Koshobu, Tokyo (JP)

(73) Assignee: JASCO Corporation, Tokyo (JP)

( * ) Notice: Subject to any disclaimer, the term of this patent is extended or adjusted under 35 U.S.C. 154(b) by 69 days.

(21) Appl. No.: 15/982,444

(22) Filed: May 17, 2018

(65) Prior Publication Data

US 2018/0335382 A1 Nov. 22, 2018

(30) Foreign Application Priority Data

May 18, 2017 (JP) .................................. 2017-98698

(51) Int. Cl.
*G01N 21/552* (2014.01)
*G01N 21/33* (2006.01)
*G02B 21/00* (2006.01)

(52) U.S. Cl.
CPC .......... *G01N 21/552* (2013.01); *G01N 21/33* (2013.01); *G02B 21/0004* (2013.01)

(58) Field of Classification Search
CPC ... G01N 21/552; G01N 21/33; G02B 21/0004
USPC .................................. 359/368, 850, 857, 861
See application file for complete search history.

(56) References Cited

U.S. PATENT DOCUMENTS 5,106,196 A * 4/1992 Brierley ................. G01N 21/55
250/339.08
5,214,286 A * 5/1993 Milosevic ................. G01J 3/02
250/339.08
6,414,311 B1 * 7/2002 Wood .................... G01N 21/552
250/339.08
10,393,656 B2 * 8/2019 Soga
2005/0088656 A1 * 4/2005 Soga ...................... G01N 21/55
356/444

(Continued)

FOREIGN PATENT DOCUMENTS

JP 2001147379 A 5/2001
JP 2006208016 A 8/2006

*Primary Examiner* — Ricky D Shafer
(74) *Attorney, Agent, or Firm* — Rankin, Hill & Clark LLP (57) ABSTRACT

To provide a total reflection measurement device that can improve a light utilization rate more than a Cassegrain type objective mirror, is capable of total reflection measurement at low magnification, and can maintain compatibility with a conventional objective mirror. The device (1) includes: a pair of plane mirrors (2a, 2b) disposed on a central axis (P1); a pair of intermediate mirrors (4a, 4b) opposing to the plane mirrors (2a, 2b), respectively; a pair of ellipsoidal mirrors (6a, 6b) opposing to the intermediate mirrors (4a, 4b), respectively; and an ATR crystal (8) provided at a position nearer to the sample side than the pair of plane mirrors (2a, 2b) on the central axis (P1). The ellipsoidal mirrors (6a, 6b) are provided so that each one focal position (C1) formed by the intermediate mirror (4a, 4b) and the plane mirror (2a, 2b) are at same position on the central axis (P1), and each another focal position (C2) formed by only the intermediate mirror (4a, 4b) are also at same position on the central axis (P1). Further, the another focal position (C2) coincides with a boundary surface between the ATR crystal (8) and the sample.

9 Claims, 5 Drawing Sheets

(56) References Cited

U.S. PATENT DOCUMENTS

2006/0164633 A1* 7/2006 Koshoubu ................. G01J 3/02
356/300
2017/0371139 A1* 12/2017 Ueda .................... G01N 21/552

* cited by examiner

TOTAL REFLECTION MEASUREMENT DEVICE

RELATED APPLICATIONS

This application claims the priority of Japanese Patent Application No. 2017-98698 filed on May 18, 2017, the disclosure of which is incorporated herein by reference in its entirety.

FIELD OF THE INVENTION

The present invention relates to a device capable of total reflection absorption spectrum measurement using an infrared light, and particularly to improvement in an objective mirror that can hold an ATR crystal.

BACKGROUND OF THE INVENTION

Attenuated total reflection measurement (also referred to as ATR) method is a method for measuring absorption property of a sample by bringing a crystal (prism) having larger refractive index than the sample into contact with the sample, and making a measurement light incident at an incident angle that total reflection occurs at its boundary surface to detect a spectrum of a total reflection light. It is suitable for analyzing a substance having high light absorption, such as a solute in an aqueous solution that is difficult to perform spectrum measurement in an infrared region. Particularly, when a microscopic part of a sample is analyzed, an infrared microspectroscopic device having a reflected light system is used.

Patent Literature 1 discloses an infrared microspectroscopic device capable of total reflection measurement. This microscopic device comprises a Cassegrain type objective mirror which holds an ATR crystal. The objective mirror comprises a main mirror comprised of a concave mirror having a hole at its center and a sub-mirror comprised of a convex mirror having a diameter smaller than the main mirror, and the main mirror and the sub-mirror are disposed oppositely with their central axes aligned with each other. Further, the ATR crystal is mounted to an end part of a holding frame and is disposed to coincide with a focusing position of the Cassegrain mirror.

Usually, only a part in contact with the sample can be subjected to total reflection measurement. However, in recent years, a method for subjecting a certain region to mapping measurement of which the ATR crystal and the sample are not relatively moved and kept in a contact state (so-called smart mapping) has become widespread. For example, like a total reflection measurement device described in Patent Literature 2, a light from a contact surface of a sample and an ATR crystal is focused by a Cassegrain mirror and is directed to a detection-side scan mirror. When the orientation of a reflection surface of the detection-side scan mirror is fixed in a certain direction, only the light from a specific part of the sample surface corresponding to the orientation of the reflection surface passes through an aperture, and the light from other parts are blocked. That is, a conjugate position on the contact surface with respect to the aperture can be changed by changing the orientation of the detection-side scan mirror. Thus, a measurement position on the contact surface can be scanned without moving the sample, so that mapping measurement can be performed to a specific region in the contact state.

CITATION LIST

Patent Literature

PATENT LITERATURE 1: Japanese Patent Publication No. JP2001-147379
PATENT LITERATURE 2: Japanese Patent Publication No. JP2006-208016

DISCLOSURE OF THE INVENTION

Problem to be Solved by the Invention

In a conventional Cassegrain type objective mirror, its sub-mirror is comprised of a convex mirror, and thus light utilization rates at focusing of the measurement light and detecting of the total reflection light were respectively poor.

That is, while the objective mirror is mounted onto an optical axis of the microscopic device, the measurement light forms an optical path in the order of the sub-mirror of the Cassegrain mirror, the main mirror of the same, and the crystal. In this case, although the measurement light which is made incident to an intersection point of the convex surface of the sub-mirror and the central axis and the vicinity thereof is reflected by the sub-mirror, the measurement light passes through a central hole of the main mirror and escapes without being incident to the concave surface of the main mirror. Even if the measurement light manages to be made incident to the concave surface of the main mirror, its reflection light proceeds in the direction other than the direction toward the crystal. Thus, the sub-mirror of the Cassegrain mirror has an incident region for the measurement light that cannot be used for measurement, and thus the utilization rate of the measurement light was insufficient.

Similarly, the total reflection light from the boundary surface between the crystal and the sample forms an optical path in the order of the crystal, the main mirror of the Cassegrain mirror, and the sub-mirror of the same. In this case, the intersection point of the convex surface of the sub-mirror and the central axis and the vicinity thereof cannot contribute to reflection of the total reflection light from the crystal. The sub-mirror of the Cassegrain mirror has a region which does not contribute to reflection of the total reflection light, and thus the utilization rate of the total reflection light is insufficient, too.

Further, an advantage of the Cassegrain type objective mirror is that its magnification is relatively high, so that the objective mirror itself can be designed compactly. However, because of its high magnification, the target region in the above-mentioned mapping measurement being narrowed was a problem. If the objective mirror having low magnification is constituted in a constitution other than the Cassegrain mirror, the objective lens itself becomes large, and compatibility with the conventional Cassegrain type objective mirror cannot be obtained.

The present invention has been accomplished in view of the above-mentioned problems, and its object is to provide a total reflection measurement device capable of improving a light utilization rate more than a Cassegrain type objective mirror, performing total reflection measurement at magnification lower than the Cassegrain type objective mirror, and maintaining compatibility with a conventional high magnification objective mirror.

Means to Solve the Problem

A total reflection measurement device according to the present invention improves a light utilization rate by disposing a pair of plane mirrors on a central axis, has low magnification focusing function by an ellipsoidal mirror, and has managed to be compact in size by an intermediate mirror.

That is, a total reflection measurement device (1) mounted to a microscopic device (10) having a reflected light system for a sample comprises:

a pair of plane mirrors (2a, 2b) disposed on a central axis (P1) as a common optical axis of a measurement light which is made incident and a total reflection light which is emitted, an intermediate mirror (4a) on the measurement light side provided at a position which receives the measurement light reflected by a plane mirror (2a) on the measurement light side of the pair of plane mirrors (2a, 2b), an intermediate mirror (4b) on the total reflection light side provided at a position opposing to a plane mirror (2b) on the total reflection light side of the pair of plane mirrors (2a, 2b) and on a side opposite to the intermediate mirror (4a) with respect to the central axis (P1), an ellipsoidal mirror (6a) on the measurement light side provided at a position opposing to the intermediate mirror (4a) on the measurement light side as an objective mirror on the measurement light side, an ellipsoidal mirror (6b) on the total reflection light side provided at a position opposing to the intermediate mirror (4b) on the total reflection light side as an objective mirror on the total reflection light side, and an ATR crystal (8) provided on the central axis (P1) at a position nearer to the sample side than the pair of plane mirrors (2a. 2b).

The ellipsoidal mirror (6a) on the measurement light side is provided so that one focal position (C1) of the ellipsoidal mirror (6a) formed by the intermediate mirror (4a) on the measurement light side and the plane mirror (2a) on the measurement light side is on the central axis (P1), and another focal position (C2) of the ellipsoidal mirror (6a) formed by the intermediate mirror (4a) on the measurement light side is on the central axis (P1) at a side closer to the sample side than the pair of plane mirrors (2a, 2b).

A boundary surface between the ATR crystal (8) and the sample coincides with the another focal position (C2) of the ellipsoidal mirror (6a).

The ellipsoidal mirror (6b) on the total reflection light side is provided so that another focal position of the ellipsoidal mirror (6b) formed by the intermediate mirror (4b) on the total reflection light side coincides with the another focal position (C2) of the ellipsoidal mirror (6a) on the measurement light side, and one focal position of the ellipsoidal mirror (6b) formed by the intermediate mirror (4b) on the total reflection light side and the plane mirror (2b) on the total reflection light side coincides with the one focal position (C1) of the ellipsoidal mirror (6a) on the measurement light side.

In a configuration described above, the measurement light passes through the one focal position (C1) and is made incident along the central axis (P1), and the ellipsoidal mirror (6a) on the measurement light side focuses the measurement light on the another focal position (C2) at the boundary surface of the ATR crystal. Simultaneously, the ellipsoidal mirror (6b) on the total reflection light side focuses the total reflection light, which is generated on the boundary surface, to the same point as the one focal position (C1) of the ellipsoidal mirror on the measurement light side along the central axis (P1).

The pair of plane mirrors is disposed on the optical axis of the microscopic device, and light in the vicinity of the central axis among the incident measurement light can be used for measurement. Further, the reflection surface in the vicinity of the central axis among the plane mirror on the total reflection light side contributes to focusing of the total reflection light. Thus, the light utilization rate can be improved more than the Cassegrain type objective mirror. In addition, the ellipsoidal mirror is used as the objective mirror instead of the Cassegrain mirror, so that total reflection measurement can be performed at a magnification lower than the Cassegrain type objective mirror. Moreover, since the intermediate mirrors are provided, the size of the device can be substantially the same as the conventional high magnification objective mirror even if the magnification is lowered.

Further, in the present device, it is preferable that the ATR crystal is provided retractably as an insertion/extraction type. In such device, total reflection measurement can be switched to reflection observation or reflection measurement by retracting the ATR crystal.

Further, in the present device, the ATR crystal is preferably a hemispherical crystal element having a light incident/exit portion formed by a part of a spherical surface. Thus, focusing action for the measurement light and the total reflection light occurs. The hemispherical crystal element includes a crystal element such as one which does not have a complete hemispherical surface, but includes at least a portion of a spherical surface. Such device uses the hemispherical ATR crystal, so that measurement magnification can be improved as the refractive index of the ATR crystal is high.

On the other hand, in the present device, the ATR crystal is preferably a crystal element having a light incident/exit portion formed of a plane surface. Such ATR crystal is referred to as a light incident/exit portion planar typed crystal element, and crystal elements such as a triangular prism type or a pentagonal prism are included, for example. In such device, the incident surface of the measurement light and the exit surface of the total reflection light in the ATR crystal are plane surfaces, so that focusing action does not occur at the ATR crystal, and low magnification measurement performed by the objective mirror can be maintained in total reflection measurement.

Around the boundary surface between the ATR crystal and the sample, the ATR crystal preferably has a tapered surface formed in an oblique angle toward the boundary surface. The tapered surface may be a slightly rounded curved surface. The tapered surface may be formed in accordance with the path of light that travels inside the ATR crystal. By providing the tapered surface around the boundary surface of the ATR crystal, a contact area between the ATR surface and the sample is not enlarged unnecessarily, and the sample can be measured in a small amount.

Figure 5:
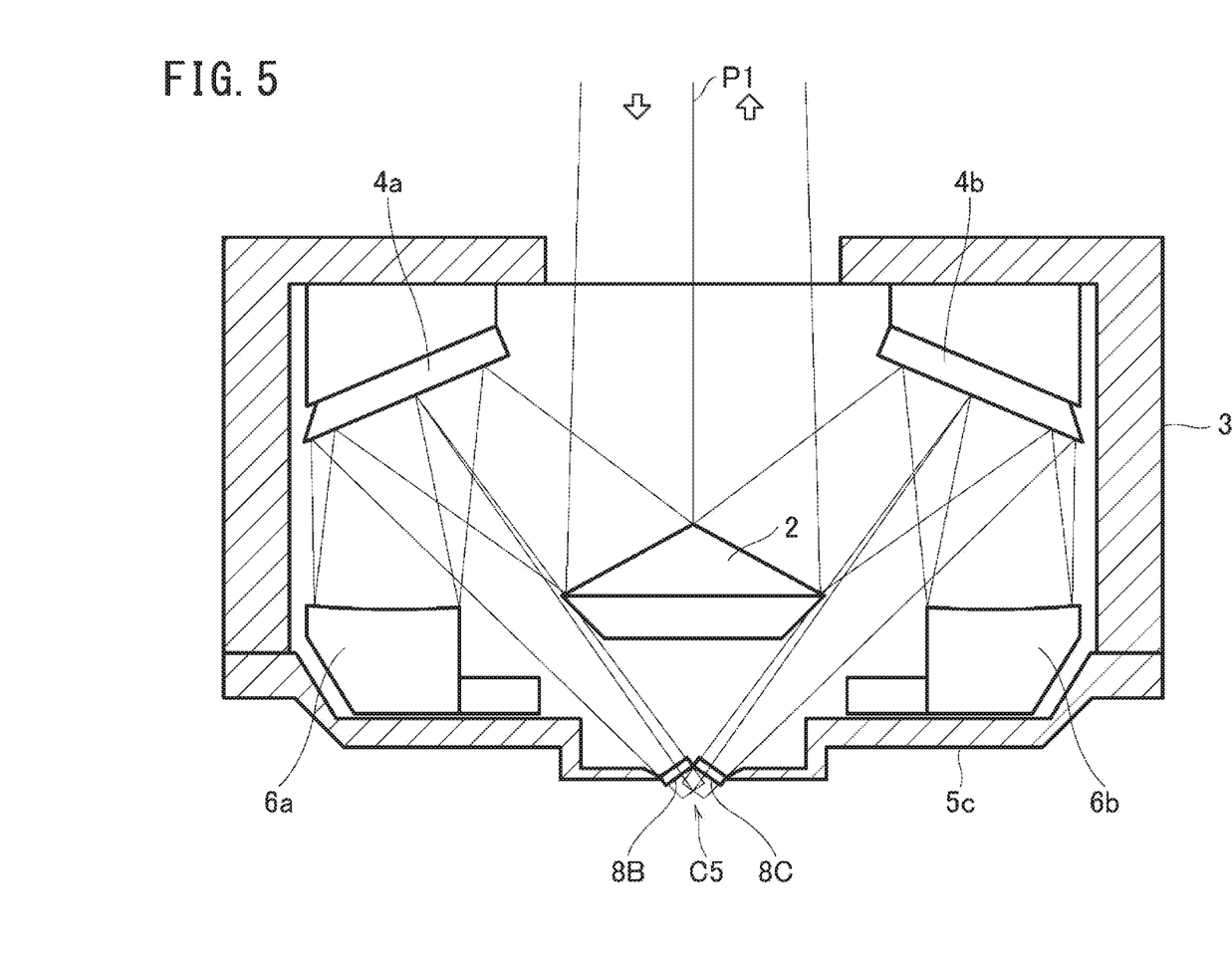
FIG. 5 is a diagram of an embodiment when the ATR device of FIG. 4 is used in reflection observation or reflection measurement.

Further, it is preferable that, instead of the ATR crystal, a pair of transparent plane plates having the same optical path length as the ATR crystal inserted at symmetrical positions with respect to the central axis in the optical paths from the intermediate mirrors to the sample. An example of such disposition of each optical element is shown in FIG. 5. Reference numbers 8B and 8C in FIG. 5 correspond to the transparent plane plates.

Figure 4:
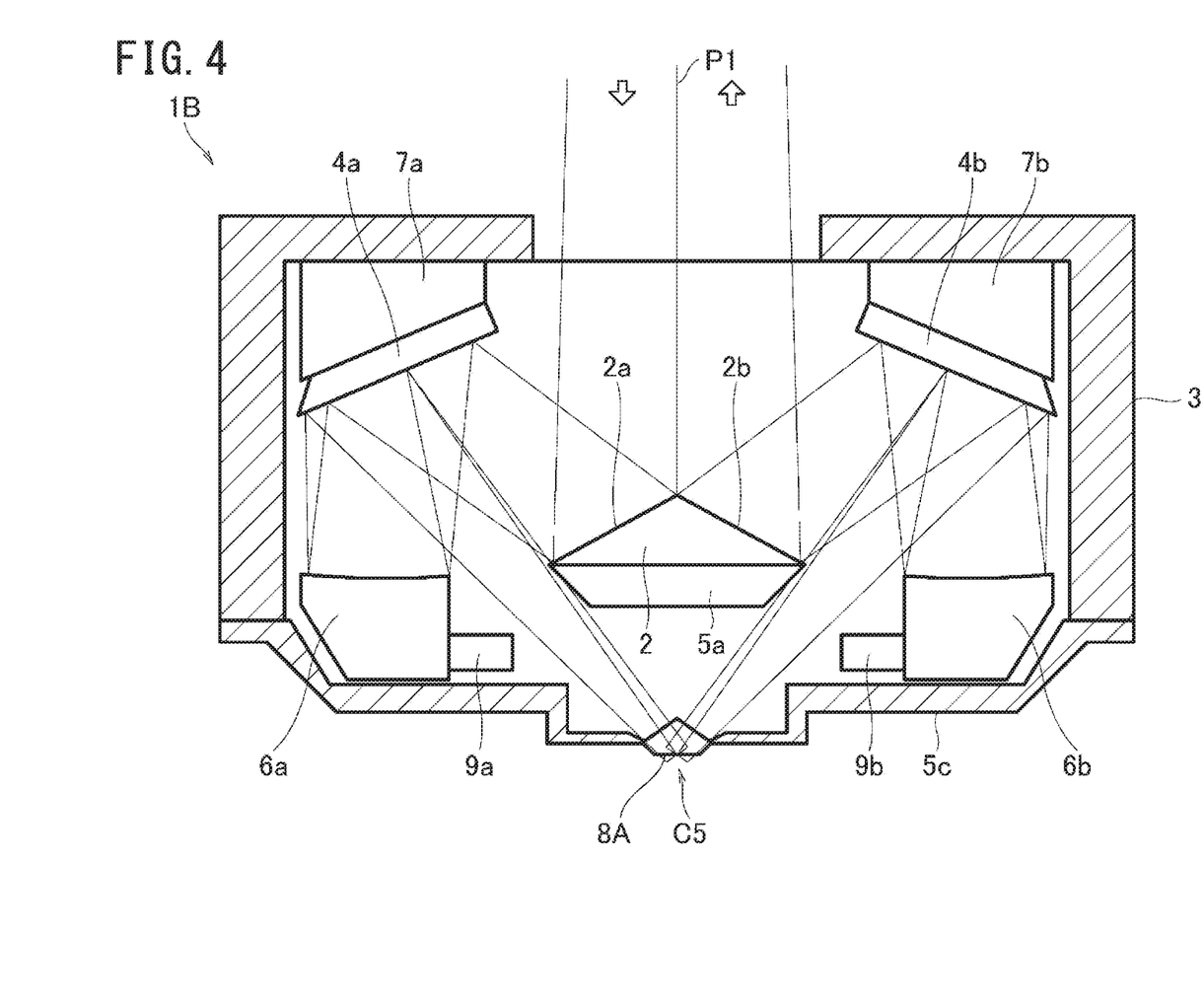
FIG. 4 is a diagram of a third used state of the ATR device of FIG. 2.

In such device, the transparent plane plates having the same optical path length as the ATR crystal are inserted at the symmetric positions with respect to the central axis instead of the light incident/exit portion planar typed ATR crystal, so that the focal positions of total reflection measurement and reflection observation (or reflection measurement) coincide. Therefore, switching from total reflection measurement to reflection observation or reflection measurement can be performed smoothly. An example of such switching is shown in FIGS. 4 and 5. Reference number 8A in FIG. 4 corresponds to the light incident/exit portion planar typed ATR crystal, and total reflection measurement is performed by using the same. Further, as shown in FIG. 5, by using the transparent plane plates 8B, 8C instead of the light incident/exit portion planar typed ATR crystal, switching from total reflection measurement to reflection observation or reflection measurement is enabled.

Effect of the Invention

In the total reflection measurement device according to the present invention, the light utilization rate can be improved more than the Cassegrain type objective mirror, so that measurement accuracy is improved. In addition, total reflection measurement can be performed at a magnification lower than the Cassegrain type objective mirror, so that measurement region for total reflection and reflection measurement becomes larger. Moreover, the size of the device can be substantially the same as in a conventional high magnification objective mirror even if magnification is lowered, so that compatibility with the high magnification objective mirror can be maintained.

BEST MODE FOR CARRYING OUT THE INVENTION

Figure 1:
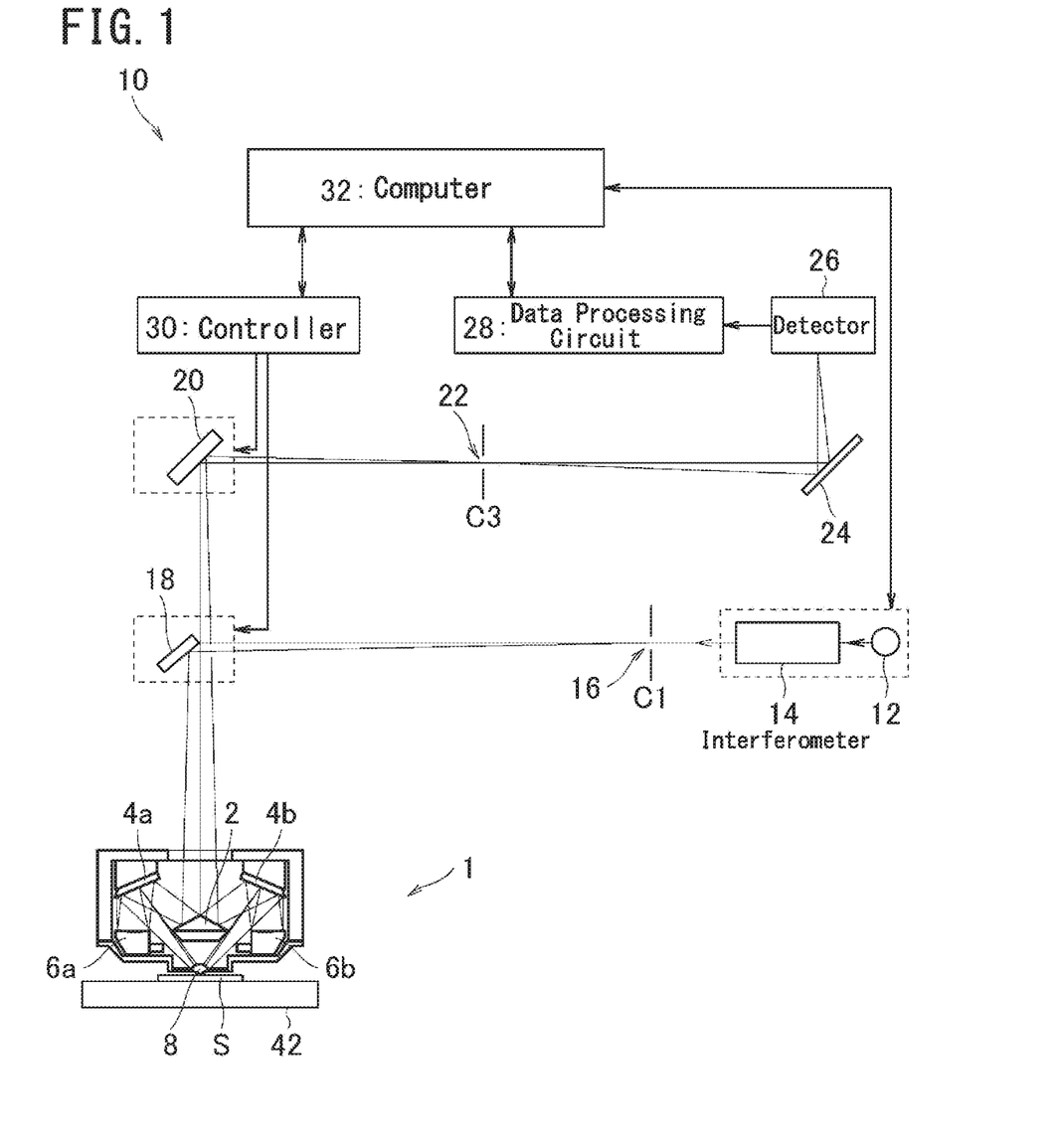
FIG. 1 is a schematic diagram of an infrared microscopic device according to one embodiment of the present invention.

Hereinbelow, a preferable embodiment of the present invention is described with reference to the figures. FIG. 1 is a schematic diagram of an infrared microscopic device on an embodiment of the present invention, and one having smart mapping function is described as an example. An infrared microscopic device 10 of the present invention comprises: an ATR device (attenuated total reflection measurement device) 1: an infrared light source 12; a Michelson interferometer 14 for generating an infrared interference light (measurement light) based on the infrared light from the light source; an irradiation-side aperture 16; an irradiation-side scan mirror 18 disposed on an optical path from the aperture 16 to the ATR device 1; an detection-side scan mirror 20 disposed on an optical path from the ATR device 1 to a detection-side aperture 22; the detection-side aperture 22 for limiting a total reflection light proceeding toward a detector 26 to light from a specific part of the sample within an abutment surface; a focusing mirror 24: and the detector 26 for detecting the total reflection light such as a linear array detector.

Figure 2:
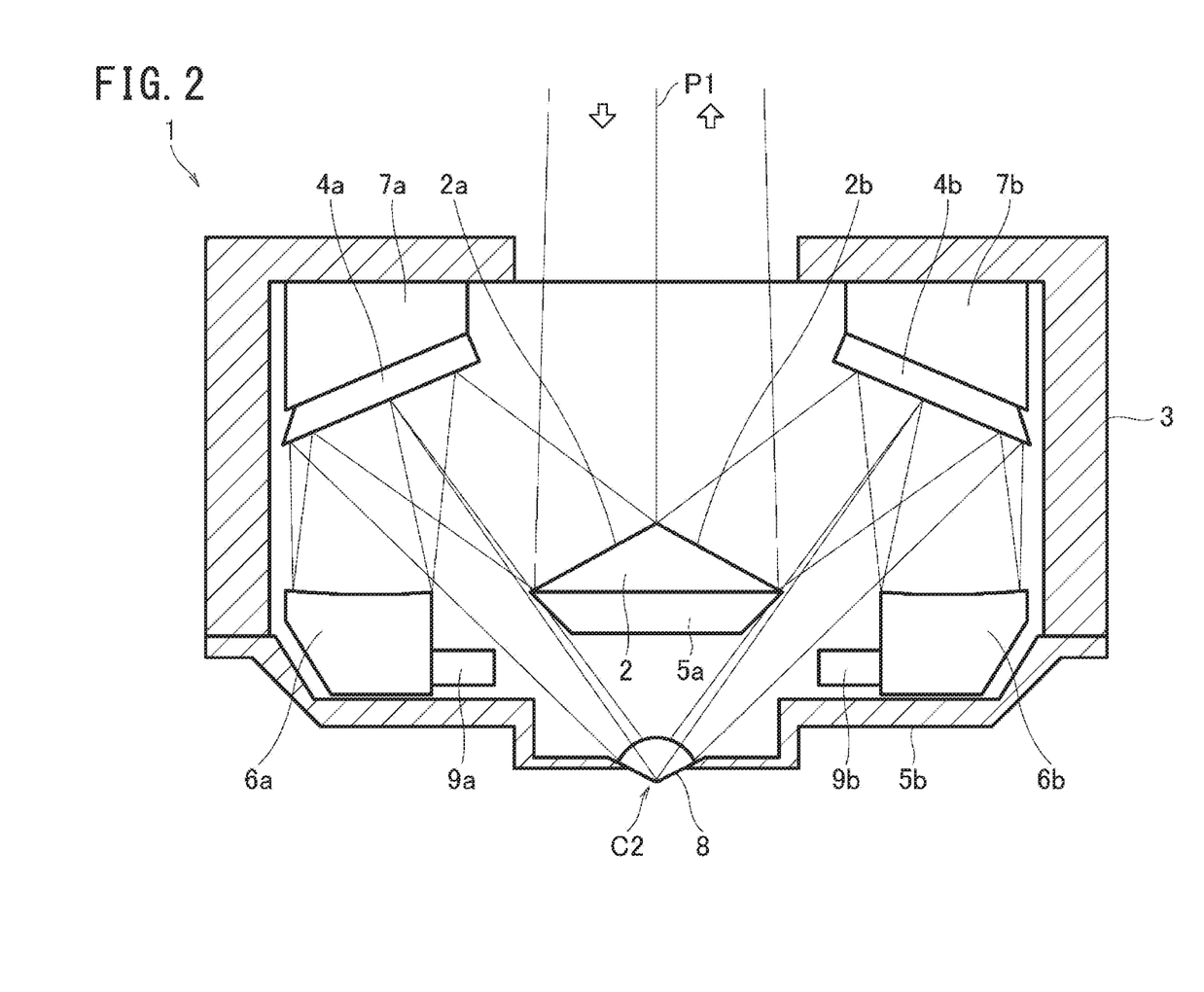
FIG. 2 is a diagram for describing an ATR device (total reflection measurement device) shown in FIG. 1.

The ATR device 1 is configured to be detachable to the infrared microscopic device. A characteristic feature of the present invention is that observation of low magnification total reflection spectrum and an object to be measured, and improvement in the light utilization rate can be performed simultaneously. Therefore, in the present embodiment, the ATR device 1 having an ellipsoidal mirror 6 as an objective mirror shown as an enlarged view in FIG. 2 is provided. The ATR device 1 has a housing 3, and is mounted to the infrared microscopic device so that its central axis P1 coincides with a common optical axis of an incident measurement light and an emitting total reflection light. A plane mirror 2 having a pair of plane mirror surfaces 2a and 2b, and an ATR crystal 8 having an almost hemispherical shape are disposed on the central axis P1. The ATR crystal 8 is disposed at a position nearer to the sample side than the plane mirror 2. The plane mirror 2 and the ATR crystal 8 are mounted to the housing 3 by mounting members 5a and 5b, respectively. The ATR crystal 8 can be disposed such that its convex surface faces toward the plane mirror 2, its central axis coincides with the central axis P1 of the ATR device, and a central point of its hemispherical surface coincides with a focal position (light convergence position) of ellipsoidal mirrors 6a and 6b, which will be described below.

The two mirror surfaces 2a and 2b of the plane mirror 2 cross at a specific angle, and has a common ridge line which is orthogonal to the central axis P1. The two mirror surfaces 2a and 2b are mounted such that their positions and postures are symmetric to the central axis P1. The measurement light from the irradiation-side scan mirror 18 is made incident to the mirror surface 2a on the measurement light side along the central axis P1. Simultaneously, the total reflection light focused by the ATR device 1 is reflected by the mirror surface 2b and emitted toward the detection-side scan mirror 20 along the central axis P1.

Further, the housing 3 has a pair of intermediate mirrors 4a and 4b mounted by mounting members 7a and 7b so that their positions and postures are symmetric to the central axis P1. Moreover, a pair of ellipsoidal mirrors 6a and 6b is mounted to the housing by mounting members 9a and 9b so that their position and posture becomes symmetric to the central axis P1. This pair of mirror bodies 6a and 6b has symmetric shapes, respectively.

First of all, optical elements that form an optical path of the measurement light from the plane mirror 2 to the ATR crystal 8 of the ATR device are described.

The plane mirror surface of the intermediate mirror 4a on the measurement light side opposes to the mirror surface 2a on the measurement light side of the plane mirror 2. Further, the ellipsoidal mirror 6a on the measurement light side has a curved mirror surface formed of a part of an ellipsoid body, and opposes to a mirror surface of the intermediate mirror 4a. The measurement light reflected by the mirror surface 2a is reflected by the intermediated mirror 4a. Then, it is further reflected by the ellipsoidal mirror 6a, and returns to the intermediate mirror 4a. The one focal position of the ellipsoidal mirror 6a on the measurement light side is formed at a position symmetric to a focal position when the intermediate mirror 4a is not disposed with respect to the mirror surface of the intermediate mirror 4a on the measurement light side, and is formed at a position symmetric to a focal position when the plane mirror 2a is not disposed with respect to the mirror surface of the plane mirror 2a on the measurement light side. The one focal position of the ellipsoidal mirror 6a on the measurement light side is formed on the central axis P1. However, in the present embodiment, the irradiation-side scan mirror 18 is disposed on the central axis P1, so that the one focal position of the ellipsoidal mirror 6a is formed at a position C1 symmetric to a focal position when the irradiation-side scan mirror 18 is not disposed with respect to the mirror surface of the irradiation-side scan mirror 18. Moreover, the focal position C1 coincides with the position of the irradiation-side aperture 16. Further, the other focal position of the ellipsoidal mirror 6a on the measurement light side is formed at a position symmetric to a focal position when the intermediate mirror 4a is not disposed with respect to the mirror surface of the intermediate mirror 4a on the measurement light side. The boundary surface between the ATR crystal 8 and the sample coincides with the other focal position C2 of the ellipsoidal mirror, so that the measurement light returned from the ellipsoidal mirror 6a to the intermediate mirror 4a is reflected by the intermediate mirror 4a and proceeds toward the ATR crystal 8.

In other words, the ellipsoidal mirror 6a on the measurement light side focuses the measurement light that passed the irradiation-side aperture 16 positioned at the one focal position C1 to the ATR crystal 8 positioned at the other focal position C2. In the ATR crystal 8, the measurement light made incident from the incident surface formed of a part of a spherical surface is subjected to focusing action of the hemispherical surface, and is focused to the central position of a circle of curvature radius, that is the contact surface with the sample.

Next, optical elements forming an optical path of the total reflection light from the ATR crystal 8 which reflects the total reflection light to outside of the ATR device 1 via the plane mirror 2 are described.

The intermediate mirror 4b on the total reflection light side is mounted at a position and posture symmetric to the intermediate mirror 4a with respect to the central axis P1. Similarly, the ellipsoidal mirror 6b on the total reflection light side is mounted at a position and posture symmetric to the ellipsoidal mirror 6a with respect to the central axis P1. Therefore, the total reflection light reflecting on the abutment surface with the sample is subjected to focusing action by the exit surface formed of a part of a spherical surface, and is reflected by the intermediate mirror 4b on the total reflection light side. Then, the total reflection light is further reflected by the ellipsoidal mirror 6b, and returns to the intermediate mirror 4b. The one focal position of the ellipsoidal mirror 6b on the total reflection light side is formed at a position symmetric to a focal position when the intermediate mirror 4b is not disposed with respect to the mirror surface of the intermediate mirror 4b on the total reflection light side, and is formed at a position symmetric to a focal position when the plane mirror 2b is not disposed with respect to the mirror surface of the plane mirror 2b on the total reflection light side. The one focal position of the ellipsoidal mirror 6b on the total reflection light side is formed on the central axis P1. However, in the present embodiment, the detection-side scan mirror 20 is disposed on the central axis P1, so that the one focal position of the ellipsoidal mirror 6b is formed at a position C3 symmetric to a focal position when the detection-side scan mirror 20 is not disposed with respect to the mirror surface of the detection-side scan mirror 20. Further, the focal position C3 coincides with the position of the detection-side aperture 22. The other focal position of the ellipsoidal mirror 6b on the total reflection light side is formed at a position symmetric to a focal position when the intermediate mirror 4b is not disposed with respect to the mirror surface of the intermediate mirror 4b on the total reflection light side. The position of this focal position coincides with the other focal position C2 of the ellipsoidal mirror 6a on the measurement light side.

Therefore, the ellipsoidal mirror 6b on the total reflection light side focuses the total reflection light reflecting on the other focal position C2 to the detection-side aperture 22 positioned at the one focal position C3. Then, the total reflection light that passed through the aperture 22 is focused by the focusing mirror 24 to be made incident to the detector 26.

The curved reflection surfaces of the ellipsoidal mirrors 6a and 6b are formed by a part of a surface of an ellipsoid body having two focal positions, respectively. When the central position on the reflection surface of the ellipsoidal mirror and each focal position thereof are joined by lines, it is preferable that an angle formed by the two lines is as small as possible. This angle corresponds to an off-axis angle of the ellipsoidal mirror 6a and 6b, and is set to 40 degrees or less, preferably 30 degrees or less. This is because imaging function is better when the off-axis angle is smaller.

As an example of the ATR crystal 8, a crystal of which its surface opposite to the surface in contact with the sample (incident/exit surface of light) is hemispherical, and the surface in contact with the sample has a reversed trapezoidal cross section (the short side of the trapezoidal shape forms the contact surface) may be used. The surface formed in an oblique direction with respect to the contact surface is referred to as a tapered surface. That is, a crystal having its portion in contact with the sample is projected is used. Further, a crystal of an almost biconvex lens shape having its two opposing curved surfaces have different radii of curvature and centers of curvature, respectively, may be used. However, the ATR crystal used in the present invention is not limited to such shapes. The material of the ATR crystal is generally Ge, ZnSe, diamond and the like.

<Realization of Total Reflection Spectrum Measurement at Low Magnification>

To measure a total reflection spectrum, an infrared interference light obtained from the interferometer 14 is reflected by the irradiation-side scan mirror 18 to form an incident light, and the light is made incident to the ATR device 1. Then, the total reflection light reflecting on the abutment surface with the sample S on an automatic stage 42 becomes an emitted light from the ATR device 1. The emitted light is reflected by the detection-side scan mirror 20, and passes through the detection-side aperture 22. Then, its light intensity is detected at the detector 26, and its detection signal is supplied to a data processing circuit 28. The data processing circuit 28 synchronizes with a sampling signal obtained separately, reads out a light intensity signal from the detector 26, and performs a publicly known signal process such as Fourier-transformation and the like to obtain an infrared absorption spectrum.

According to such configuration, the ellipsoidal mirrors 6a and 6b having small off-axis angles are adopted as the objective mirror, so that spectrum measurement at a low magnification of about 2 to 8 times can be realized. Further, a group of optical elements (a pair of intermediate mirrors 4a and 4b, and a pair of ellipsoidal mirrors 6a and 6b) of the ATR device 1 is disposed on the plane parallel to paper surface of FIG. 1, and a plurality of pixels of the linear array detector 26 are aligned in a direction orthogonal to paper surface of FIG. 1. Thus, on the contact surface of the ATR crystal 8 and the sample, several points corresponding to each pixel of the linear array detector 26 are also aligned in a direction orthogonal to paper surface of FIG. 1. Further, the optical elements are disposed on the plane orthogonal to the alignment direction of the points corresponding to each pixel, so that a high imaging performance at the linear array detector 26 can be realized.

Further, the light utilization rate is increased by disposing the plane mirror 2 on the central axis P1. Therefore, by disposing a multi aperture at a focal position of the microscopic optical system or the FTIR optical system, spatial resolution can be improved while maintaining sufficient amount of light. Further, since the light utilization rate becomes extremely high, appropriate spectrum can be obtained even when a TGS detector is used.

Moreover, even if magnification is lowered, the size of the device can be almost the same as the conventional objective mirror having high magnification by providing the intermediate mirrors 4a and 4b. Therefore, compatibility with the conventional objective mirror having high magnification can be maintained.

Figure 3:
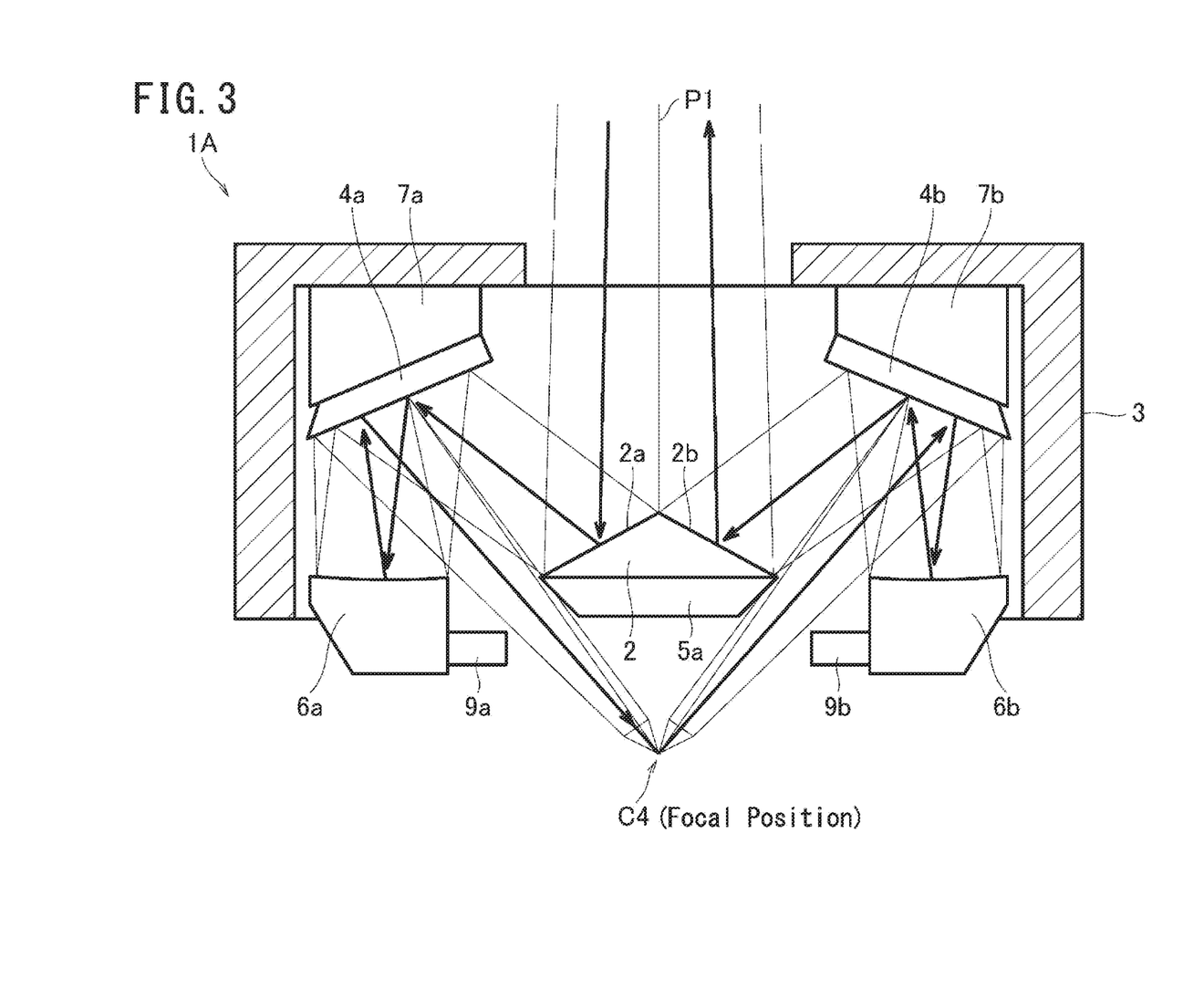
FIG. 3 is a diagram of a second used state of the ATR device of FIG. 2.

FIG. 3 shows a configuration of the ATR device 1A in a state which the mounting member 5b for the crystal at the bottom of the ATR device 1 in FIG. 2 is removed. By only removing the ATR crystal 8, the measurement light is focused to a focal position C4. The focal position C4 is at a same position as the focal position C2 when the ATR crystal 8 is disposed. The measurement light can be focused to the focal position C4 of the ellipsoidal mirror 6a by finely adjusting the position and the posture of each optical element mounted to the ATR device 1A, so that it becomes an objective mirror applicable for reflection measurement of the sample. Thus, the configuration of the ATR device of the present invention is capable of providing an objective mirror applicable for low magnification reflection measurement and low magnification ATR measurement.

<Realization of Mapping Measurement for a Wide Field of Vision>

The infrared microscopic device 10 of the present embodiment has mapping measurement function. The orientation of the reflection surface of the irradiation-side scan mirror 18 is controlled by a controller 30, and a measurement portion (imaging position of the measurement light) can be moved variously. Further, the total reflection light from the ATR device 1 is sent to the detection-side scan mirror 20. The detection-side scan mirror 20 reflects the total reflection light from the sample and sends it to the detection-side aperture 22. The orientation of the reflection surface of the detection-side scan mirror 20 is also controlled by the controller 30, and only the light from a selected measurement portion is directed to an opening of the detection-side aperture 22. The detection-side aperture 22 blocks the reflection light from portions other than the measurement portion, and transmits the light only from the measurement portion. Thus, a conjugate position in the abutment surface with respect to the detection-side aperture 22 can be changed.

Therefore, measurement is repeated by changing the orientations of the reflection surfaces of the irradiation-side scan mirror 18 and the detection-side scan mirror 20 respectively, so that two-dimensional mapping measurement of the abutment surface region of the ATR crystal 8 and the sample surface can be performed without changing the abutment position of the ATR crystal with respect to the sample. Moreover, the ellipsoidal mirrors 6a and 6b having small off-axis angles are adopted as objective mirrors, so that surface analysis for a wide field of view at low magnification of about 2 to 8 times can be realized and imaging measurement for a wide region can be realized while the ATR crystal 8 is in contact with the sample. For example, an imaging range can be increased from 100 μm square to 2000 μm square, and this is an extremely epoch-making extension.

<Realization of Further Low Magnification Analysis>

FIG. 4 shows a configuration of an ATR device 1B when an ATR crystal 8A having a planar typed light incident/exit portion held by a mounting member 5c is adopted instead of the hemispherical ATR crystal 8. The crystal 8A having a planar typed light incident/exit portion has an incident surface of the measurement light and an exit surface of the total reflection light formed by plane surfaces. Same optical elements as the ATR device 1 in FIG. 2 are used to finely adjust positions and postures of each optical element, so that the measurement light can be focused to a focal position C5 of the ellipsoidal mirror 6a. Moreover, the abutment surface of the ATR crystal 8A having a planar typed light incident/exit portion and the sample is made coincident with the focal position C5, so that total reflection measurement at magnification of the ellipsoidal mirror 6a (for example, 4 times) can be performed.

The ATR crystal 8A has tapered surfaces formed in oblique directions with respect to the boundary surface around the boundary surface (abutment surface) with the sample. The entire shape of the ATR crystal 8A is a square pillar having pentagonal cross sections. The tapered surface is formed in accordance with a path of light travelling inside the ATR crystal 8A. By providing the tapered surfaces around the boundary surface of the ATR crystal 8A, the contact area of the ATR crystal 8A and the sample is not enlarged unnecessarily, and the sample can be measured in a small amount.

<Smooth Switching of Total Reflection Measurement and Reflection Measurement at Low Magnification>

FIG. 5 shows a configuration of the ATR device of which a pair of transparent plane plate 8B and 8C having the same optical path length as the crystal having a planar typed light incident/exit portion of FIG. 4 mounted by a mounting member 5d instead of the crystal of FIG. 4. In the optical path from the intermediate mirrors 4a and 4b to the sample, the transparent plane plates 8B and 8C are inserted at symmetric positions with respect to the central axis P1.

In such device, the pair of transparent plane plate 8B and 8C having the same optical path length as the ATR crystal 8A having the planar type light incident-exit portion are inserted, so that measurement portions for total reflection measurement and reflection measurement (focal position of the measurement light) coincide at a position C5. Therefore, switching from total reflection measurement to reflection measurement or reflection observation can be performed smoothly, and both of low magnification reflection measurement and low magnification ATR measurement can be realized.

In the present embodiment, examples that uses the Fourier transformation typed spectrometer are shown, but dispersing type spectrometer may be used. Further, the spectrometer is disposed on the light irradiation means side in the examples, but it can be disposed on the light detection means side.

Further, it is preferable that the ATR crystal is provided retractably as an insertion/extraction type. By retracting the ATR crystal as the insertion/extraction type, switching from total reflection measurement to reflection observation or reflection measurement becomes easily.

A plurality of objective mirrors having low magnification and high magnification may be mounted to a revolver, so that the objective mirror is selectable. The objective mirror can be selected desirably by the revolver, which makes it easy to use.

Further, although the microscopic device of the present invention has mapping measurement function, the total reflection measurement device according to the present invention can be effectively applied as a measurement device not only for such surface analysis, but for point analysis too.

DESCRIPTION OF REFERENCE NUMBERS 1, 1A, 1B ATR device (Total reflection measurement device)
2 Plane mirror 4a, 4b Intermediate mirror
6a, 6b Ellipsoidal mirror
8, 8A ATR crystal (ATR prism)
10 Infrared microscopic device

What is claimed is:

1. A total reflection measurement device mounted to a microscopic device having a reflected light system for a sample comprises:
   a pair of plane mirrors disposed on a central axis as a common optical axis of a measurement light which is made incident and a total reflection light which is emitted,
   an intermediate mirror on the measurement light side provided at a position which receives the measurement light reflected by a plane mirror on the measurement light side of the pair of plane mirrors,
   an intermediate mirror on the total reflection light side provided at a position opposing to a plane mirror on the total reflection light side of the pair of plane mirrors and on a side opposite to the intermediate mirror on the measurement light side with respect to the central axis,
   an ellipsoidal mirror on the measurement light side provided at a position opposing to the intermediate mirror on the measurement light side as an objective mirror on the measurement light side,
   an ellipsoidal mirror on the total reflection light side provided at a position opposing to the intermediate mirror on the total reflection light side as an objective mirror on the total reflection light side, and
   an ATR crystal provided on the central axis at a position nearer to the sample side than the pair of plane mirrors,
   wherein the ellipsoidal mirror on the measurement light side is provided so that one focal position of the ellipsoidal mirror formed by the intermediate mirror on the measurement light side and the plane mirror on the measurement light side is on the central axis, and another focal position of the ellipsoidal mirror formed by the intermediate mirror on the measurement light side is on the central axis at a side closer to the sample side than the pair of plane mirrors;
   a boundary surface between the ATR crystal and the sample coincides with the another focal position of the ellipsoidal mirror; and
   the ellipsoidal mirror on the total reflection light side is provided so that another focal position of the ellipsoidal mirror formed by the intermediate mirror on the total reflection light side coincides with the another focal position of the ellipsoidal mirror on the measurement light side, and one focal position of the ellipsoidal mirror formed by the intermediate mirror on the total reflection light side and the plane mirror on the total reflection light side coincides with the one focal position of the ellipsoidal mirror on the measurement light side.

2. The total reflection measurement device according to claim 1, wherein the ATR crystal is provided retractably as an insertion or extraction type.

3. The total reflection measurement device according to claim 2, further comprising a pair of transparent plane plates having a same optical path length as the ATR crystal is inserted at symmetrical positions with respect to the central axis in the optical paths from the intermediate mirrors to the sample instead of the ATR crystal.

4. The total reflection measurement device according to claim 1, wherein the ATR crystal is a hemispherical crystal element having a light incident or exit portion formed by a part of a spherical surface.

5. The total reflection measurement device according to claim 4, wherein the ATR crystal has a tapered surface around the boundary surface formed in an oblique angle toward the boundary surface.

6. The total reflection measurement device according to claim 4, further comprising a pair of transparent plane plates having a same optical path length as the ATR crystal inserted at symmetrical positions with respect to the central axis in the optical paths from the intermediate mirrors to the sample instead of the ATR crystal.

7. The total reflection measurement device according to claim 1, wherein the ATR crystal is a crystal element having a light incident or exit portion formed of a plane surface.

8. The total reflection measurement device according to claim 7, wherein the ATR crystal has a tapered surface around the boundary surface formed in an oblique angle toward the boundary surface.

9. The total reflection measurement device according to claim 7, further comprising a pair of transparent plane plates having a same optical path length as the ATR crystal inserted at symmetrical positions with respect to the central axis in the optical paths from the intermediate mirrors to the sample instead of the ATR crystal.

* * * * *